(12) United States Patent
Patel et al.

(10) Patent No.: US 6,696,261 B2
(45) Date of Patent: Feb. 24, 2004

(54) PYROGENICITY TEST FOR USE WITH AUTOMATED IMMUNOASSAY SYSTEMS

(75) Inventors: Mehul Patel, Erie, CO (US); Stephen Poole, London (GB)

(73) Assignees: Baxter International Inc., Deerfield, IL (US); National Institute for Biological Standards and Control, Hertfordshire (GB)

( * ) Notice: Subject to any disclaimer, the term of this patent is extended or adjusted under 35 U.S.C. 154(b) by 314 days.

(21) Appl. No.: 09/727,561

(22) Filed: Dec. 1, 2000

(65) Prior Publication Data

US 2001/0034037 A1 Oct. 25, 2001

Related U.S. Application Data

(60) Provisional application No. 60/168,972, filed on Dec. 3, 1999.

(51) Int. Cl.[7] ............................................. G01N 33/53
(52) U.S. Cl. ..................................... 435/7.24; 435/7.94
(58) Field of Search ............................... 435/7.24, 7.94

(56) References Cited

U.S. PATENT DOCUMENTS

| | | |
|---|---|---|
| 4,434,237 A | 2/1984 | Dinarello |
| 5,128,270 A | 7/1992 | Delacroix et al. |
| 5,281,540 A | 1/1994 | Merkh et al. |
| 5,891,728 A | 4/1999 | Wendel et al. |

FOREIGN PATENT DOCUMENTS

| | | | |
|---|---|---|---|
| WO | 93/02361 | * | 2/1993 |
| WO | WO 94/10571 A1 | | 5/1994 |

OTHER PUBLICATIONS

Cruse et al, Illustrated Dictionary of Immunology, CRC Press, Inc; pp 83, 248, 1995.*
Fujiwara, et al., "Measurement of Endotoxin in Blood Products Using an Endotoxin–Specific *Limulus* Test Reagent and Its Relation to Pyrogenic Activities in Rabbit." Yakugaku Zasshi, vol. 110, No. 5, pp. 332–340, 1990. (English abstract).
Desch, et al., "Production of Human Tumor Necrosis Factor from Whole Blood Ex Vivo." Lymphokine Research, vol. 8, No. 2, pp. 141–146, 1989.
Harris, et al., "Detection of Endotoxin in Triglyceride–Rich Lipoproteins in vitro." The Journal of Laboratory and Clinical Medicine, vol. 118, No. 2, pp. 186–193, 1991.
Taktak, et al., "Assay of Pyrogens by Interleukin–6 Release from Monocytic Cell Lines." Journal of Pharmacy & Pharmacology, vol. 43, No. 8, pp. 578–582, 1991.
Finch–Arietta, et al., "Cytokin Production in Whole Blood Ex Vivo." Agents and Actions, vol. 34, No. 1/2, pp. 49–52, 1991.
Emancipator, et al., "In Vitro Inactivation of Bacterial Endotoxin by Human Lipoproteins and Apolipoproteins." Infection and Immunity, vol. 60, No. 2, pp. 596–601, 1992.
Zeisberger, et al. "Neurobiological Concepts of Fever Generation and Suppression." Neuropsychobiology, vol. 28, pp. 106–109, 1993.
Read, et al., "The Protective Effect of Serum Lipoproteins Against Bacterial Lipopolysaccharide." European Heart Journal, vol. 14, pp. 125–129, 1993.
Moltz. H., "Fever: Causes and Consequences." Neuroscience and Biobehavioral Reviews, vol. 17, No. 3, pp. 237–269, 1993.
Rothwell, N., "CNS Regulation of Thermogenesis." Neurobiology, vol. 8, Issues 1,2, pp. 1–10, 1994.
Tilders, et al., "Activation of the Hypothalamus–Pituitary–Adrenal Axis by Bacterial Endotoxins: Routes and Intermediate Signals." The Official Journal of the International Society of Psychoneuroendocrinology, vol. 19, No. 2, pp. 209–232, 1994.
Medgenix pdate, "TNF α And Multiple Sclerosis." May 1995.
Cytotrap™–IL–6 DIA, Cytokine stimulation Assay, Protocol for an incubation of 24 hours, Aug. 5, 1999.
DynaMiX—TNF—α—DIA, Cytokin Stimulation Assacy Protocol for an incubation of 3 hours, May 7, 1997.

* cited by examiner

Primary Examiner—David Saunders
(74) Attorney, Agent, or Firm—Senniger, Powers, Leavitt & Roedel (57) ABSTRACT

The invention concerns an improved pyrogenicity test for use in automated immunoassay systems, in which a sample is incubated with a monocyte-containing reagent in a pyrogen-free assay system preferably comprising a surface coated with pyrogen-free anti-cytokine antibodies. The invention also concerns pyrogen-free assay systems coated with pyrogen-free antibodies for use in these tests. The invention also relates to a test to measure the basal production of endogenous mediators of the inflammatory response by leukocytes and a method of measuring the capacity of a leukocyte to respond to a stimuli.

20 Claims, 6 Drawing Sheets

PYROGENICITY TEST FOR USE WITH AUTOMATED IMMUNOASSAY SYSTEMS

CROSS-REFERENCE TO RELATED APPLICATION

This application claims priority from Provisional Application Ser. No. 60/168,972 filed on Dec. 3, 1999, which is hereby incorporated by reference in its entirety.

FIELD OF THE INVENTION

The invention concerns an improved pyrogenicity test for use in automated immunoassay systems, in which a sample is incubated with a monocyte-containing reagent in a pyrogen-free assay system comprising a surface preferably coated with pyrogen-free anti-cytokine antibodies. The invention also concerns pyrogen-free assay systems coated with pyrogen-free antibodies for use in these tests. The invention also relates to a test to measure the basal production of endogenous mediators of the inflammatory response by leukocytes and a method of measuring the capacity of a leukocyte to respond to a stimuli.

BACKGROUND OF THE INVENTION

When certain chemical or biological compounds are brought into contact with the circulatory system of humans or other mammals, they cause a systemic response characterized by an elevation in body temperature, or fever. Such materials are called "pyrogens" or "pyrogenic" compounds. Compounds which pose a particular risk of pyrogenicity include medical products which can be inhaled, injected or infused, and medical devices such as membranes or implanted materials. Even nutrients can represent a risk of pyrogenicity. In addition to the pyrogenic nature of the product itself or by-products of its production, bacterial contamination of the product can often cause pyrogenicity. This problem persists even if the product is "sterilized" by heat or chemical methods, as the main pyrogenic component of the bacteria, endotoxin (or cell wall lipopolysaccharide), can remain after the bacteria are killed.

Usually, compounds which act as a pyrogen do so by stimulating cytokine production in monocytes after contact with tissue, cells or body fluids. It is these endogenously produced cytokines which produce the fever response in the affected organism. The most important known fever producing cytokines are the proteins interleukin-1 (IL-1), interleukin-1ra (IL-1ra), interleukin-6 (IL-6), interleukin-8 (IL-8) and tumor necrosis factor (TNF), as well as low molecular weight lipid mediators such as prostaglandin $E_2$ ($PGE_2$). These compounds are routinely assayed by ELISA, or enzyme-linked immunosorbent assays (for IL-1, IL6, or TNF), and EIA, or enzyme immunoassay (for $PGE_2$).

In order to avoid a pyrogenic reaction and ensure the safety of any drug or pharmaceutical product administered parenterally, pyrogenic contamination must be monitored to identify individual lots that are contaminated with bacteria. Two pharmacopial methods, the Limulus amebocyte lysate (LAL) test and the rabbit pyrogen test, are currently used routinely to monitor pyrogen contamination in mass-produced pharmaceutical products.

The rabbit test is an in-vivo test which consists of injecting a statistically significant number of rabbits with the compound, and observing the average rise in body temperature elicited in the test animals. Although the rabbit test is responsive to a wide spectrum of pyrogenic agents, including bacterial endotoxin, the rabbit test has a relatively low sensitivity (ng endotoxin/ml) compared to other pyrogen tests (pg endotoxin/ml for the LAL test). In addition, the correlation between species of pyrogenic responses to compounds is, at best, rough. It has been documented, for instance, that the dose of bacterial endotoxin eliciting a pyrogenic response varies as much as 10,000 times between species. Rabbit tests have the further disadvantage of taking one to two days to administer properly. The expense, relative insensitivity, and ethical issues involved in animal testing have made the rabbit test disfavored in recent years.

Among the compounds causing fever, one of the best described is endotoxin (lipopolysaccharide, LPS), which comes from the bacterial wall of Gram-negative germs (Moltz et al., Neurosci. Biobehav. Rev., 1993, 17, 237–269; Tilders et al., Psychoneuroendocrinology, 1994, 19, 209–232; Rothwell, Crit. Rev. Neurobiol., 1994, 8, 1–10; Zeisberger and Roth, Neuropsychobiology, 1993, 28, 106–109). It was, therefore, thought to be generally useful to replace expensive and time consuming rabbit experiments with a direct LAL test for endotoxin. This approach has obvious limitations. The LAL test is a very sensitive in-vitro test; however, it only detects endotoxins from Gram-negative bacteria and gives false negative results with certain products which can still stimulate monocytes to make pyrogenic cytokines. The LAL test is also altered by endotoxin-binding components that are present in blood or blood components (Harris et al, J. Lab. Clin. Med., 1991, 118, 186–193; Emancipator et al., 1992, Infect. Immun., 60, 596–601; Read et al., Eur. Heart J., 1993, 14, 125–129). Some of these endotoxin-binding components bind to LPS and prevent it from being detected. These components may also affect the immune reaction with monocytes, i.e., the primary pyrogenic reaction. This interference is problematic, as testing for exogenous pyrogens in blood products is essential in order to ensure safe administration of these products in the clinical setting. On the other hand, the Limulus test is so sensitive that it is easily prone to false positive results due to impurities that are not relevant to product quality (Fujiwara et al., Yakugaku Zasshi, 1990, 110, 332–340).

It has been observed that cytokines are produced by whole blood when endotoxin is added, ex vivo. After incubation of whole blood with *Sal. minnesota* lipopolysaccharide for six hours, an increase in IL-1 β and TNF-α could be detected in the culture by ELISA. (M. B. Finch, et al., "Cytokine Production In Whole Blood ex vivo," Agents & Actions 34:49–52 (1991), C. E. Desch, et al., 'Production of Human Tumor Necrosis Factor from Whole Blood Ex Vivo," Lymphokine Rsrch, 8:141–46 (1989)). In addition, cultured monocyte cell lines have also been observed to produce IL-1 β and IL-6 when incubated with *E. coli* endotoxin, and it has been suggested that such cell lines can be used as an effective pyrogen test.(Taktak et al., "Assay of Pyrogens by Interleukin-6 Release from Monocytic Cell Lines," J. Pharm. Pharmacol. 143:578–582 (1991)).

U.S. Pat. No. 5,891,728 describes a method of bringing a sample of potentially pyrogenic material into contact with human whole blood to release cytokines from monocytes and other white blood cells. An advantage of this procedure is that the use of a complete biological reagent (whole blood) allowed assessment of the exposure of humans and other mammals to pyrogenic agents in the test sample. All blood components that are needed for an interaction of the exogenous pyrogen with leukocytes (e.g., LPS binding protein—LBP, soluble CD 14, etc.) are present. After incubation of the sample with whole blood in a test container, the incubation mixture is centrifuged, clarified, and assayed for the presence of secreted cytokines in a separate immunoassay step.

Although this test method is an improvement over the LAL test, and potentially detects a large variety of potential exogenous pyrogens other than endotoxin, it has several disadvantages which prevent or severely limit its use on an industrial scale. The two separate steps of culturing the blood with test material and assaying the culture for cytokine production are done in separate containers, requiring the cultured material to be transferred to a new container for immunoassay. The transfer of material necessitated by these separate steps is not easily done utilizing modem quality control assay equipment. Pyrogen tests are normally (and preferably) carried out simultaneously, testing numerous lots of pharmaceutical products for pyrogen contamination. Thus, a need exists for a pyrogenicity test which can be carried out in a single, assay container system, and which combines the steps of sample incubation with the pyrogen-detecting biological reagent and the capture of cytokine(s) produced by the biological reagent.

SUMMARY OF THE INVENTION

Applicants have developed an in-vitro pyrogen test that is very sensitive, detects any pyrogens capable of producing a fever response (i.e. endotoxins from Gram-negative and Gram-positive bacteria and non-lipopolysaccharide materials), and is inexpensive. Generally, the present invention is drawn to a method of detecting pyrogens in a sample by incubating the sample with a monocyte-containing reagent in a pyrogen-free assay system comprising a surface coated with pyrogen-free anti-cytokine antibodies, and assaying the assay system for the presence of cytokines bound to the surface by the coating antibodies.

In preferred embodiments of the present invention, the monocyte-containing reagent comprises whole blood, such as whole human blood. The monocyte-containing reagent may further comprise an anticoagulant or a diluent or both.

In preferred embodiments of the pyrogen test of the present invention, the cytokine assayed for in the assay system is interleukin-1, interleukin-1ra, interleukin-6, interleukin-8, tumor necrosis factor-$\alpha$, or prostaglandin $E_2$.

In preferred embodiments of the pyrogen test of the present invention, the assay system is a microtiter well, and the surface on which the antibody is coated is a portion of the interior of the microtiter well.

In preferred embodiments of the pyrogen test of the present invention, the pyrogen-free assay system is assayed by a calorimetric enzyme-linked immunosorbent assay for cytokine bound to the anti-cytokine antibody coated on the surface of the assay system.

The present invention is also drawn to a pyrogen-free assay system comprising a surface coated with pyrogen-free anti-cytokine antibodies. In preferred embodiments of the invention, the assay system is a microtiter well wherein a pyrogen-free antibody to a cytokine is coated on a portion of the interior of the microtiter well. In more preferred embodiments, the well is part of a planar array of similar wells, situated so that the array of wells may be read with automated immunoassay plate reading equipment. In preferred embodiments of assay system of the present invention, the cytokine to which the antibodies bind is interleukin-1, interleukin-1ra, interleukin-6, interleukin-8, tumor necrosis factor-$\alpha$, or prostaglandin $E_2$.

DEFINITIONS

As used herein, the term "pyrogen-free" means substantially free of pyrogen contaminants so that background cytokine production is sufficiently reduced to enable the desired detection sensitivity for the particular application of the method of the invention. The amount of allowable pyrogen contamination in the assay systems of the present invention will thus vary with the particular item being tested. For instance, blood products and solutions for large volume injection must have very low levels of pyrogen (<0.25 EU/ml). Thus, when the method of the present invention is used to test these products, the assay system cannot have more than 0.06 EU/ml container volume of pyrogen contaminants. For general use in screening pharmacological materials for injection, a pyrogen-free assay system preferably has no more than 0.25 EU/ml container volume of pyrogen contaminants, more preferably no more than 0.06 EU/ml container volume of pyrogen contaminants, more preferably no more than 0.03 EU/ml container volume of pyrogen contaminants, and most preferably no more than 0.0125 EU/ml container volume of pyrogen contaminants.

The term "monocyte-containing reagent" means any solution of monocytic leukocyte cells of the immune system. Preferably, these cells are derived from the organism to whom the product which is being tested is to be administered (i.e., human for pharmaceutical products, cat, dog, horse, etc. for veterinary products). An example of a monocyte-containing reagent is whole human blood.

The term "leukocyte-containing reagent" means any solution of leukocyte cells of the immune system. An example of a leukocyte-containing reagent is whole human blood.

The term "assay system" means any container and surface with bound antibody which may be used in an immunoassay. Preferably, such containers are microtiter well plates with antibody bound to a surface in the well, in which a large number of colorimetric enzyme-linked immunoassays may be carried out in parallel and which may be automatically evaluated by an ELISA plate reading machine. However, other systems are envisioned, especially those where the coated surface is not necessarily part of the wall of the container. For instance, a larger test tube which contains a polystyrene bead or dipstick coated by the antibody could be used in the present invention.

DETAILED DESCRIPTION OF THE INVENTION

Pyrogens stimulate blood monocytes (as well as other leukocytes) and macrophages to produce and release numerous endogenous pyrogenic mediators of the inflammatory response, including cytokines (e.g. TNF-$\alpha$, IL-1$\beta$, and IL-6). The release of these pyrogenic mediators into the circulation triggers a cascade of events leading to a fever response in the affected individual. The in-vitro pyrogen test of the present invention relies on the measurement of these endogenous pyrogens as a marker for a fever response. In the preferred pyrogen test of the present invention, a sample is incubated with a monocyte-containing reagent in a pyrogen-free assay system comprising a surface coated with pyrogen-free anti-cytokine antibodies, and the assay system is assayed for the presence of cytokines bound to the surface by the coating antibodies.

Figure 4:
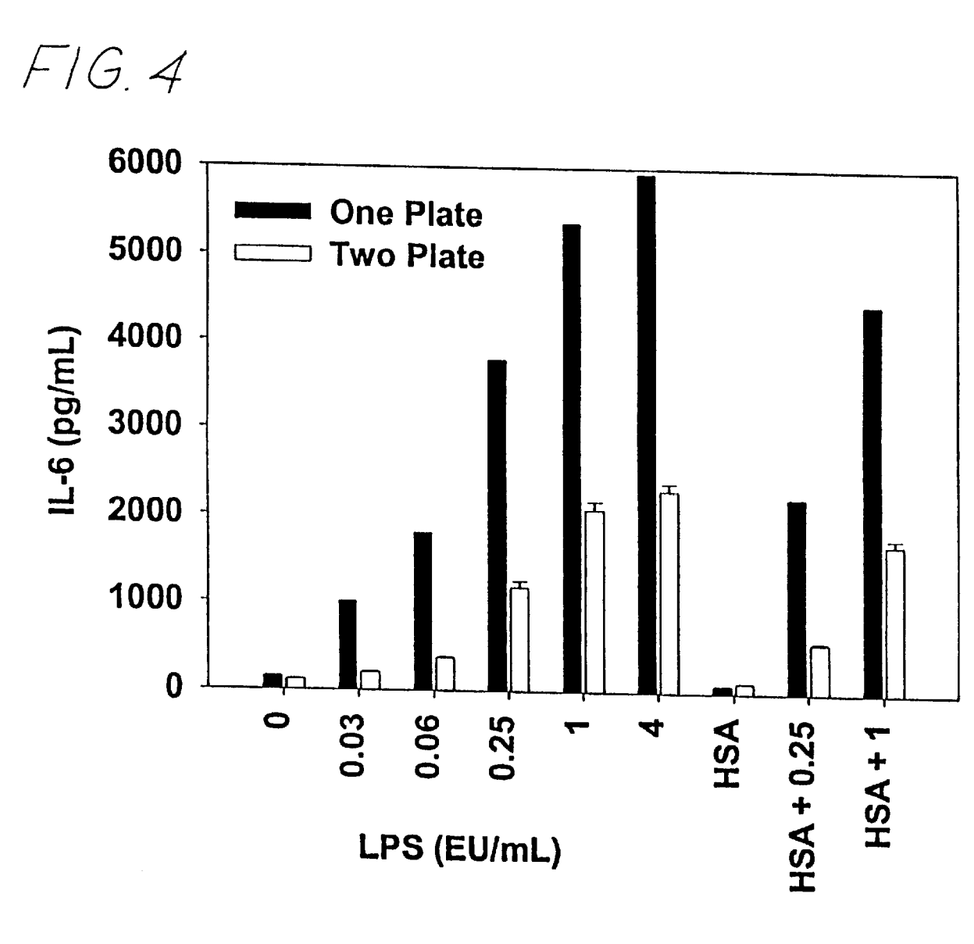
FIG. 4: A chart of the IL-6 response of ex vivo whole human blood stimulated with USP endotoxin as described in Example 5. Blood from a single donor was diluted to a final concentration of about 20%, and an incubation time of 4 hours was used. This chart compares the results obtained with the "two plate" assay described in U.S. Pat. No. 5,891,728 and the "one plate" assay of the present invention. As shown by these results, the one plate assay is much more sensitive than the two plate assay, when performed under similar conditions.

The pyrogen test of the present invention has been shown to be more sensitive than the "two plate" assay previously described, see FIG. 4. At the limit of detection of the LAL test, 0.03 EU/ml, the two plate test produces an IL-6 increase which is barely detectable over the background (0 EU/ml). However, the pyrogen test of the present invention produces a clear, detectable increase in IL-6 at 0.03 EU/ml. These results indicate, by interpolation, that even 0.01 EU/ml is detectable using the test of the present invention. The ability of the test to detect minimal levels of pyrogen is important, as product samples are often diluted for testing, in order to conserve product and prevent product interference with the test. The more sensitive the test, the greater the "maximum valid dilution" of the test sample. In addition, the test of the present invention allows better detection of endotoxin contamination in blood products. As HSA is a major component of many blood products, the ability of a test to detect pyrogen contamination in HSA samples as indicated by "spike recovery" of the IL-6 signal when endotoxin is added, see FIG. 4, indicates that the test of the present invention would be well suited for use in testing blood products.

Any endogenous mediator of the inflammatory response secreted by the monocyte-containing reagent that is detectable may be used as the basis of the pyrogen test of the present invention. Preferably, however, a cytokine or endothelin marker will be employed because due to their size, they are easy to detect by the method of the invention. It has been found that monocytes in whole blood incubated with bacterial endotoxin produce several classes of cytokines, including, but not limited to pro-inflammatory cytokines (TNF-$\alpha$, IL-1, IL-6), anti-inflammatory cytokines (IL-4, IL-10, IL-13, IL-1ra, TGF), Th1 (IL-2, IFN, IL-12), Th2 (IL-4, IL-5, IL-6, IL-10, IL-13), IL-1$\beta$, IL-1ra, IL-8 and PGE$_2$. Preferred cytokine markers for use in the invention include TNF-$\alpha$, IL-1$\beta$, IL-1ra, IL-6, IL-8 and PGE$_2$. IL-6 is a particularly preferred cytokine marker to assay in the present invention. IL-6 is produced in detectable amounts within a relatively short incubation period when endotoxin is the pyrogenic agent (see FIG. 2 and FIG. 5). Immunoreactive IL-6, unlike immunoreactive IL-1$\beta$ and TNF$\alpha$, is secreted entirely into the cell-conditioned medium/blood, in large quantities, permitting its complete estimation. In contrast, immunoreactive TNF$\alpha$ and IL-1$\beta$ remain largely intracellular, raising the possibility that test preparations affecting cell-permeability might more easily interfere in the test with (immunoreactive) TNF$\alpha$ or IL-1$\beta$ as the readout, rather than IL-6. Nevertheless, TNF-$\alpha$ or IL-1$\beta$ could also be used as a cytokine marker in the present invention. TNF-$\alpha$ is produced earlier than IL-6 in the monocyte pyrogen response. Thus, an embodiment of the invention which assays TNF-$\alpha$ would use a shorter incubation time (~1 hour) than embodiments which assay IL-6. Different pyrogenic contaminants may elicit different cytokine responses in the cell culture. Therefore, the invention may be tailored to detect the formation of particular cytokines when contamination with a particular pyrogen which causes secretion of those cytokines is probable for a pharmaceutical product.

Once the cytokine to be assayed has been determined, a pyrogen-free antibody to that cytokine must be made for use in the present invention. Polyclonal antibodies purified under stringent conditions, as outlined in Example 1, work well in the pyrogen test. Because the animal blood from which the polyclonal antibodies are isolated is naturally pyrogen-free (if taken from healthy animals), one must simply prevent contamination of the raw materials with pyrogens during purification to obtain a pyrogen-free product. Pyrogen-free buffers and solid phases are used in affinity chromatography columns to obtain pyrogen-free polyclonal antibodies as described in Example 1. Alternatively, monoclonal antibodies from hybridoma cultures could be used. However, when using monoclonal antibodies, one must be particularly careful to isolate the antibodies from any contaminating pyrogen which may be present in the hybridoma cell culture.

For use in the present invention, the pyrogen-free antibody to the cytokine is applied to a surface in a pyrogen-free assay system. Methods, such as coating, for binding antibodies onto a surface in an assay system, such as a microtiter well, are well known in the biochemical arts. Many assay systems are available commercially, and the manufacturer usually provides materials and instructions for coating antibodies onto a surface of the system. Because of their ease of reading and the small sample volume required, microtiter wells in which a portion of the interior surface of the well is coated by the antibody are used in a preferred embodiment of the present invention. In order to fully exploit the advantages of the invention, it is preferred that the microtiter well be part of a microtiter plate, which is a planar array of similar wells, situated so that the array of wells may be read with automated immunoassay plate reading equipment (see, e.g., U.S. Pat. No. 5,281,540, hereby incorporated by reference). Automated equipment such as ELISA plate readers (e.g., the Ultramark Microplate Reader, available from Bio-Rad Laboratories, Inc.), automate the assay evaluation process and greatly decrease the per-test cost. Microtiter well plates are rendered pyrogen-free (if not already supplied as such) and suitable for coating with pyrogen-free antibody for use in the present invention by extensive washing with pyrogen-free buffer. In a particularly preferred embodiment of the present invention, pyrogen-free anti-IL-6 polyclonal antibodies are coated onto the wells of an ELISA plate. However, other immuno-diagnostic test formats (e.g., in which the pyrogen-free antibody is coated on a dipstick or bead) are acceptable for use in the present invention.

In addition to the "capture" antibody, other pyrogen-free antibodies and reagents for use in assaying the cytokine may be applied when making pyrogen-free microtiter plate systems for use in the present invention. For instance, after the pyrogen-free capture antibody is applied to the microtiter plate, the remaining binding sites of the plate can be "blocked" with another protein. After blocking, a pyrogen-free labeled detection antibody (such as a biotinylated antibody) can be applied to the microtiter plate, along with a protective glazing compound. Thus, when a sample is incubated in the microtiter well, as described below, the released cytokine is captured by the pyrogen-free capture antibody bound to the well and labeled by the detecting antibody simultaneously during the sample incubation period.

As the first step in the pyrogen test of the present invention, a monocyte-containing reagent and the sample being tested are incubated in the assay system. The monocytes in the monocyte-containing reagent preferably are monocytes from the same species to whom the product tested is to be administered (i.e., human for pharmaceutical products; cat, dog, horse, etc. for veterinary products). However, monocytes from other species with the desired pyrogen reactivity may also be used. A preferred embodiment of the in-vitro pyrogen test uses whole blood as the monocyte-containing reagent. Preferably, blood for use as a monocyte-containing reagent in the present invention is fresh, or less than 24 hours old, and more preferably less than 4 hours old. Solutions of monocytes isolated from whole blood could be used as a biological reagent in the present invention. However, isolation procedures may prime for cytokine production by the monocytes, which can lead to false positive results. As another alternative, solutions of cultured monocyte cell lines may be used in the present invention. However, these monocyte cell lines tend to respond less vigorously than whole blood to pyrogen stimulation, and can lose their cytokine secreting behaviors after several dozen generations. It is, therefore, preferred to use human or animal whole blood as the monocyte-containing reagent for use in the invention. When whole blood is used, the monocytes are in their natural environment and all serum components which may influence their response to pyrogens are present in solution. Anticoagulants may be used to retard or prevent blood clotting. Suitable anticoagulants include citrate (to a final concentration of 0.38%), heparin (sodium heparinate), or fragmin (low molecular weight heparin). Anticoagulant additives can be used without affecting the response of the monocytes to pyrogens in the test sample.

In preferred embodiments, the whole blood is diluted with an appropriate pyrogen-free buffer or other diluent, such as RPMI cell culture media or physiological saline. Whole blood is preferably diluted to at least 50%, more preferably to about 5% to about 25%, and more preferably about 20% of the final volume for incubation (see FIG. 1). By diluting whole blood, the IL-6 response curve of the majority of donors may be brought within a compact range that can be used to quantify a wider range of pyrogen contamination concentrations (see FIG. 3).

During the incubation step, any laboratory equipment or reagent used should be pyrogen-free. Any pyrogen contamination at this stage of the test procedure can lead to false positive results. Preferably, rigorous, sterile conditions are maintained at all points in the procedure before the antibody coated surface is assayed for bound cytokine. Incubation of test article with the monocyte-containing reagent (such as heparinized whole blood) is performed directly in the pyrogen-free assay system. The optimal incubation time for use in the pyrogen test of the present invention will vary depending on the cytokine which is assayed. For IL-6, minimal additional cytokine is produced by the monocyte-containing reagent after incubation for 6 hours (see FIG. 2). After 4 hours of incubation, a sufficient amount of IL-6 has been secreted by the reagent to allow quantification of the pyrogen contaminant. Thus, for an embodiment of the present invention which assays IL-6 production, an incubation time of about 4 hours is preferred. If another cytokine is assayed, the incubation period should be optimized for the production of that particular cytokine. Such optimization is within the abilities of the person of ordinary skill in the art. If the cytokine to be assayed is not released by the monocytes, a detergent may be added at the end of the incubation period to lyse the cells.

Once the incubation is completed, the assay system is assayed for the presence of cytokine on the surface coated with the pyrogen-free anti-cytokine antibody. If an ELISA plate coated with a capture antibody is used as the embodiment of the present invention, the plate is washed, and a second anti-cytokine antibody conjugated with an enzyme is added to the ELISA plate (unless the second, labeled, 'detecting' antibody was initially added to the plate before glazing or together with the test material or standard endotoxin prior to tissue culture). The ELISA plate is washed again, and addition of a substrate to the ELISA plate will produce a color. After a short incubation time, the reaction is terminated, and the optical density of the solution is measured on an ELISA plate reader. This process is further described in Example 2. Alternatively, non-enzymatic immunoassay techniques may be used. For instance, the second antibody of the immunoassay "sandwich" may be labeled with a fluorescent moiety or a radioactive isotope. After washing, the amount of cytokine captured in the well can be quantified by detecting the amount of fluorescence or radiation present in the well. Several enzymatic and non-enzymatic based assay systems are available commercially, and can be easily modified for use in the present invention by one of ordinary skill in the art.

In order to properly interpret the cytokine production data generated in the pyrogen test of the present invention, an endotoxin standard curve is generated by incubating the monocyte-containing reagent with USP standard endotoxin. The purpose of this is to quantify the cytokine production response measured for a test sample in terms of the response observed for a known endotoxin. A standard curve may be generated from any statistically significant number of data points generated with significantly varied concentrations of standard endotoxin by utilizing standard best-fit data analysis software. Methods of generating such standard curves are generally known in the art. Applicants have found that data points of 10, 4, 1, 0.25, 0.06, 0.03, and 0 EU/ml of endotoxin are suitable for generating a standard curve, but any statistically significant number of concentrations through a similar range would be suitable. Once a standard curve is generated, the equivalent endotoxin concentration may be interpolated from the cytokine response using the standard curve. As the response of whole blood-based monocyte-containing reagents can vary significantly from donor to donor (see FIG. 3), it is important to generate a standard curve for each set of assays performed with a particular lot of monocyte-containing reagent. However, because the preferred ELISA plate embodiment of the invention utilizes very small amounts of human blood (about 40 $\mu$L/well), a single unit of donated blood can be used for several hundred tests. The standard curve generated using the USP endotoxin aids in the normalization of the data in terms of relating to endotoxin units (EU, as defined by the USP/FDA, which are identical to IU, international units as defined by WHO), which is the industry standard for expressing pyrogen contamination.

The present procedure is highly sensitive to endotoxin. Picogram per ml amounts of endotoxin are able to effect the release of cytokines by the monocyte-containing reagent. However, pyrogens other than endotoxin are also detected using the test of the present invention. For instance, Gram-positive bacteria (e.g., *Staphylococcus aureus*) or their components (e.g., muropeptide, lipoteichoic acid, enterotoxins, streptolysin) are detected, as well as immune stimulators such as phytohemagglutimin or phorbolester. Because the test utilizes the cytokine response of monocytes to diverse pyrogens rather than being only Gram-negative bacterial endotoxin specific reaction, a wide spectrum of pyrogenic agents can be detected with the test of the present invention.

The one-plate assay method of the present invention may be employed in any application that utilizes the two-plate assay. In a preferred embodiment, however, the method is used to test a variety of products for pharmaceutical use. The test is especially suitable for testing blood products and other pharmaceutical products for injection or infusion, such as buffered saline. Other medicaments for injection, such as vaccines, are also suitable for testing with the method of the present invention.

The test method of the invention may also be utilized to evaluate leukocyte function and to diagnose certain immune system mediated diseases. In one embodiment, a leukocyte-containing reagent is monitored for the basal production of various endogenous mediators of the inflammatory response under study. As utilized herein "basal production" shall mean production of endogenous mediators of the inflammatory response by leukocytes not subjected to pyrogenic challenge. The leukocyte-containing reagent, preferably whole blood from a donor whose leukocytes are being evaluated, along with pyrogen-free detecting antibodies are incubated in a pyrogen-free assay system, in which a surface has been coated with pyrogen-free antibodies to the endogenous mediators of the inflammatory response under study (as set-forth in greater detail above). The pyrogen-free assay system is then assayed for endogenous mediators of the inflammatory response bound to the pyrogen free antibody and the basal production of the mediator is determined by comparing its concentration to control samples by any method generally known in the art.

The detection of the basal production of endogenous mediators of the inflammatory response may be employed in a number of applications. In a preferred application, the basal production of IL-6 in a leukocyte-containing reagent is measured. The concentration of IL-6 is generally higher in blood from a donor that has recently been, or is currently subjected to a viral or bacterial infection than blood from a donor not subjected to viral or bacterial infection. Consequently, the measurement of IL-6 by the method of the invention provides a means to rapidly determine whether a donor is, or has been, challenged by viral or bacterial infection. In yet another preferred application, the basal production of Th1 and Th2 cytokines in a leukocyte-containing reagent is monitored. Th1 cytokines mediate cell-based immunity and Th2 cytokines mediate antibody-based immunity. The balance of Th1 and Th2 cytokines can determine susceptibility to and resolution of infectious diseases, and certain infectious agents have evolved the capacity to manipulate the host's Th1/Th2 balance, a process known as "Th1/Th2 switching". Numerous diseases, including, but not limited to, asthma, rheumatoid arthritis, periodontal disease, leprosy and leishmaniasis involve Th1/Th2 switching. Accordingly, the ability to rapidly quantify levels of Th1 and Th2 cytokines by the method of the invention allows valuable information to be obtained about the Th1/Th2 status of an individual and the likely outcome of diseases that involve Th1/Th2 switching.

In yet another embodiment, the leukocyte-containing reagent may also be challenged with a stimulus and then monitored for production of endogenous mediators of the inflammatory response. In this embodiment, the leukocyte-containing reagent, preferably whole blood from a donor whose leukocytes are being evaluated, along with pyrogen-free detecting antibodies are incubated in a pyrogen-free assay system, in which a surface has been coated with pyrogen-free antibodies to the endogenous mediators of the inflammatory response under study (as set-forth in greater detail above). The stimulus may either be pre-coated onto the surface or added to the leukocyte-containing reagent and then applied to the surface and the stimulus is preferably LPS, an infectious agent (e.g. a live or dead bacteria, virus or parasite), a vaccine/adjuvant, or drug. The pyrogen-free assay system is then assayed for endogenous mediators of the inflammatory response bound to the pyrogen free antibody. The method may be employed to monitor a donor's immune response to any stimulus, but is especially suitable for profiling the donor's cytokine response when challenged with a particular stimulus. For example, the method may be used to predict a donor's susceptibility to septic/endotoxic shock based upon the donor's cytokine profile, because if stimulation by LPS results in the release of large amounts of TNF-$\alpha$ relative to IL-1 (approximately 10:1), then this suggests the likelihood of the donor developing septic shock as a consequence of a severe bacterial infection. Equally, the method may also be employed to predict the mechanism of vaccine, adjuvant, or drug action based upon a donor's cytokine profile, because a vaccine, adjuvant or drug stimulating the response of large amounts of immunoreactive Th2 cytokines and few Th1 cytokines, is likely to stimulate a better antibody response than one which has the opposite effect.

In addition, the test method disclosed can also be modified for other uses wherein a measure of a response of cells to a chemical stimulus is desired. In many bioassays, contamination of the cell culture with pyrogens can "activate" the cells, initiating a diverse cascade of cell reactions and products, preventing the detection of a marker analyte. In this embodiment of the invention, the bioassay cell culture and sample are incubated in a pyrogen-free assay system, in which a surface has been coated with a pyrogen-free antibody to a non-cytokine analyte. The cells are then lysed (if the analyte is not released by the cells), and the pyrogen-free assay system is assayed for analyte bound to the pyrogen-free antibody.

EXAMPLES

The following examples illustrate the present invention. All reagents used herein were cell culture tested, certified pyrogen-free by the supplier, or sterile filtered. Buffers used were as follows:

| PBS coating buffer, pH 7.2–7.4 | | Store at +4° C. for up to 2 months |
|---|---|---|
| NaCl | 0.14 M | (8.18 g/L) |
| KCl | 2.7 mM | (0.20 g/L) |
| $KH_2PO_4$ | 1.5 mM | (0.20 g/L) |
| $Na_2HPO_4$ | 8.1 mM | (1.15 g/L anhydrous $Na_2HPO_4$, 1.44 g/L $Na_2HPO_4.2H_2O$, 2.90 g/L $Na_2HPO_4.12H_2O$) |
| Wash/dilution buffer, pH 7.2 | | Store at +4° C. for up to 2 months |
| NaCl | 0.5 M | (29.22 g/L) |
| $NaH_2PO_4$ | 2.5 mM | (0.39 g/L of $NaH_2PO_4.2H_2O$) |
| $Na_2HPO_4$ | 7.5 mM | (1.07 g/L anhydrous $Na_2HPO_4$, 1.33 g/L $Na_2HPO_4.2H_2O$, 2.69 g/L $Na_2HPO_4.12H_2O$) |
| Adjust to pH 7.2, then add Tween 20 to 0.1% (v/v) (1.0 ml/L) | | |
| Substrate buffer, pH 5.0 | | Store at +4° C. for up to 2 months |
| Citric acid | 34.7 mM | (7.30 g/L) |
| $Na_2HPO_4$ | 66.7 mM | (9.47 g/L anhydrous $Na_2HPO_4$, 11.92 g/L $Na_2HPO_4.2H_2O$) |
| Adjust pH to 5.0 with 1 M NaOH. | | |

Example 1

Production of Pyrogen-Free Anti-Cytokine Antibody Coated ELISA Plates

Goats were immunologically challenged with IL-6 and bled according to the procedure in Taktak et al., "Assay of Pyrogens by Interleukin-6 Release from Monocytic Cell Lines," *J. Pharm. Parmacol.* 143:578–582 (1991), incorporated herein by reference. Polyclonal goat anti-human IL-6 antibodies were purified by affinity chromatography on an Affi-Gel 15 (BioRad) column (1 mL) coupled to 1 mg of IL-6 (360 µg/mL) in phosphate buffered saline (0.1 M, pH 7.4, PBS) using pyrogen-free wash buffer and elution buffer. At all times during the purification procedure, rigorous conditions were maintained to minimize possible pyrogen contamination. The fractions were neutralized with pyrogen-free 1M sodium bicarbonate. The antibodies were concentrated on a Gyrocent-L centrifugal concentrator. The solution of coating antibodies was tested for endotoxin contamination in an LAL test (<0.03 EU/ml).

Non-sterile, 96-well microtiter plates (Dynex Tech, Inc.) were rinsed extensively with pyrogen-free PBS. Plates were coated with pyrogen-free goat anti-human IL-6 antibodies (1 µg/ml, in pyrogen-free PBS, 100 µl/well, +4° C., overnight). Plates were washed twice with sterile PBS+0.1% Tween 20, then once with sterile PBS (without Tween). A blocking/glazing solution (100 µl/well of either sterile trehalose, 2%+sterile HSA, 1% or sterile sucrose, 5%+sterile HSA, 1%, in pyrogen-free PBS was added for one hour at room temperature. After one hour, the blocking/glazing solution was carefully decanted and the plates were air-dried in a Class II 'sterile' cabinet for at least four hours (usually overnight) and sealed in plastic bags and stored at 4° C. Preparation of plates under sterile conditions minimized potential contamination with pyrogens. Plates prepared in this manner were pyrogen-free.

Example 2

Assay of Pyrogen Content in Samples Spiked with Endotoxin: Comparison of Whole Blood Reagent Concentration Whole human blood (diluted, to give about 50% or 20% blood in the final test volume, with RPMI) from a single healthy donor was stimulated with endotoxin (LPS) to produce IL-6. Final test volume was 200 µL/well. Samples were incubated overnight at 37° C. Test samples used to stimulate diluted whole human blood were prepared by spiking pyrogen-free diaspirin crosslinked hemoglobin (DCLHb®) with endotoxin (ENDOTOXIN STD. USP, 2000 EU/ml) at 2.5 and 10 EU/ml and then diluting 1/10 to give 0.25 and 1.0 EU/ml 'final' concentrations for testing. For the standard curve, endotoxin without HSA was used.

At the end of the incubation plates were aspirated to remove blood cultures and washed three times with wash/dilution buffer (WDB). 100 µl/well biotinylated goat anti-IL-6 antibodies were added (diluted 1:1000 in WDB containing 1% normal goat serum) and incubated for one hour at room temperature with gentle mixing. 100 µl/well avidin-horseradish peroxidase (HRP) (diluted to manufacturer's instructions in WDB) was added for 15 min at room temperature. 100 µl/well OPD, Sigma, (200 µM tablet dissolved in 50 ml substrate buffer, 20 µl 30% $H_2O_2$ added immediately before use) was added for 10–20 min (until sufficient color developed). 1M $H_2SO_4$ (100 µl/well) was added to stop the reaction. Optical densities were read at 490 nm.

Figure 1:
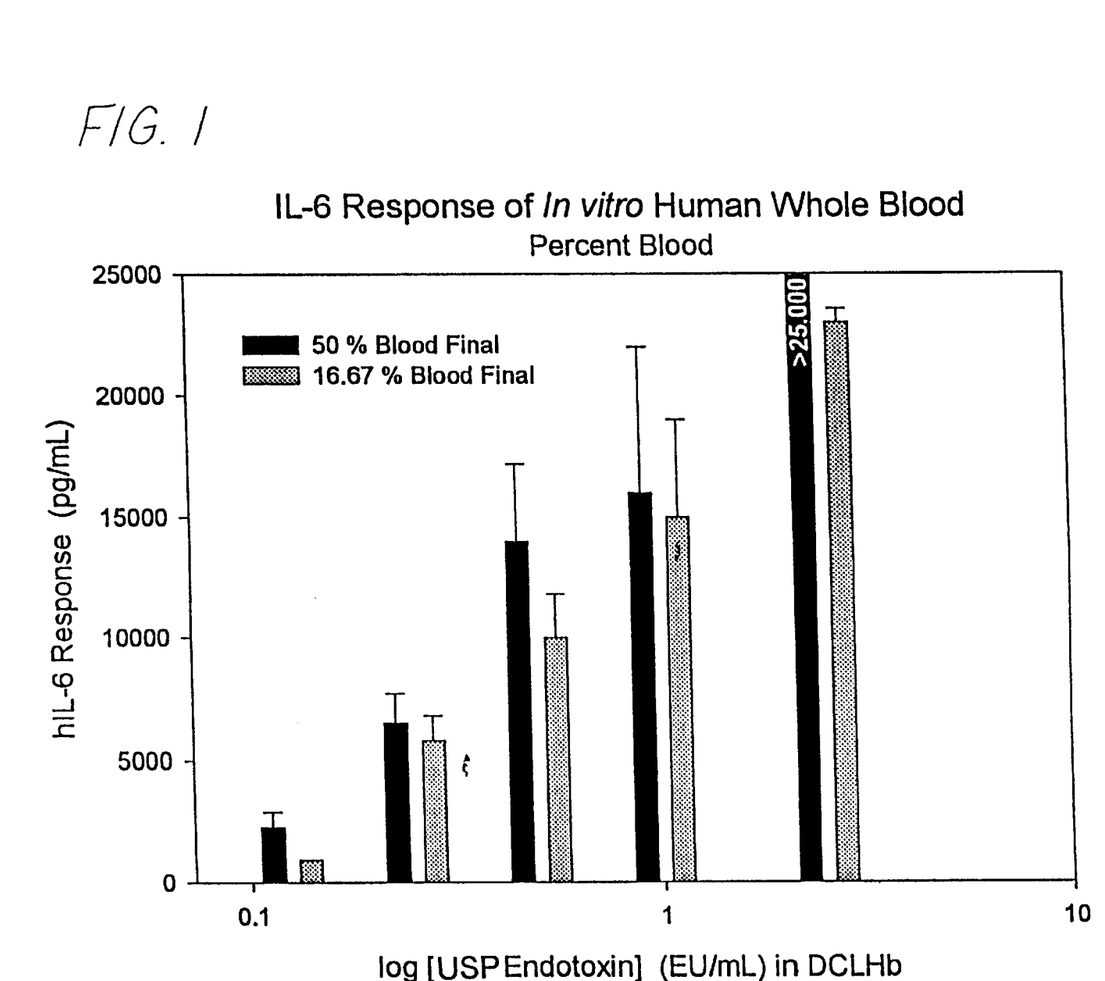
FIG. 1: A chart of the IL-6 response of ex vivo whole human blood stimulated with USP endotoxin as described in Example 2, except that diaspirin crosslinked hemoglobin (DCLHb)® was used instead of human serum albumin in the test samples. The samples were incubated overnight, and blood from a single donor was used. This chart shows the effect of final blood concentration on the test sensitivity. Although a more vigorous response to very low endotoxin samples is seen in the 50% final volume test, the 20% final volume test provides a comparable response over a wide range of endotoxin concentrations.

Results are shown in FIG. 1. Although a more vigorous response to very low endotoxin samples is seen in the 50% final volume test, the 20% final volume test provides a comparable response over a wide range of endotoxin concentrations. Thus, in order to conserve the amount of whole blood used as a reagent, it is preferred that whole blood be diluted to about 20% test volume for use in the present invention. It has also been found that a dilution to 10% test volume works well in the present invention.

Example 3

Assay of Pyrogen Content in Samples Spiked with Endotoxin: Comparison of Whole Blood Reagent Donors The test was carried out as in Example 2, except that final whole blood concentration was about 20% in the test volume, endotoxin in RPMI was used as the test samples, and blood from three healthy donors was used.

Figure 2:
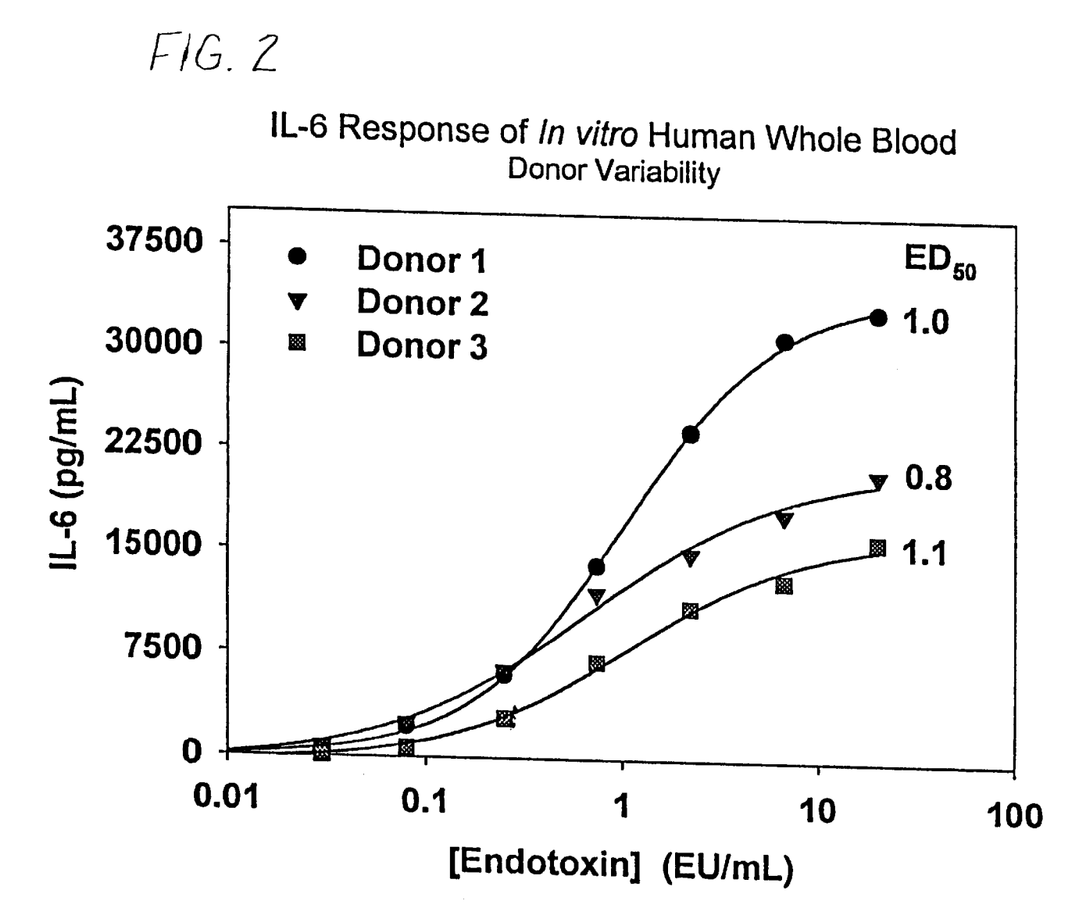
FIG. 2: A chart of the IL-6 response of ex vivo whole human blood stimulated with USP endotoxin as described in Example 3. Blood from three donors was diluted to a final concentration of about 20%, and the samples were incubated overnight. This chart shows the donor effect on the test method of the present invention. Although the absolute amount of IL-6 generated by whole human blood incubations from different donors varies considerably (by 100% at high endotoxin concentrations), the shape of the dose-response curve is very similar for all donors. This chart illustrates the importance of generating a standard curve from known endotoxin concentrations in order to interpret the data generated by the method of the invention, or by any method which utilizes whole human blood as a reagent.

Results are shown in FIG. 2. Although the absolute amount of IL-6 generated by whole human blood incubations from different donors varies considerably (by 100% at high endotoxin concentrations), the shape of the dose-response curve is very similar for all donors. This chart illustrates the importance of generating a standard curve from known endotoxin concentrations in order to interpret the data generated by the method of the invention, or by any method which utilizes whole human blood as a reagent. Because the preferred ELISA plate embodiment of the invention utilizes very small amounts of human blood (about 40 µL/well), a single unit of donated blood can be used for several hundred tests in addition to the required standard curve data. It is notable that the whole blood from all three donors produced a measurable IL-6 response when incubated with endotoxin, indicating that the majority of donor blood should be suitable for use as a reagent in the present invention.

Example 4

Assay of Pyrogen Content in Samples Spiked with Endotoxin: Comparison of Incubation Times The test was carried out as in Example 2, except that final whole blood concentration was about 20% in the test volume, endotoxin in RPMI was used as the test samples, and incubation times of 2, 4, 6, 8, 20, and 24 hours were used.

Figure 3:
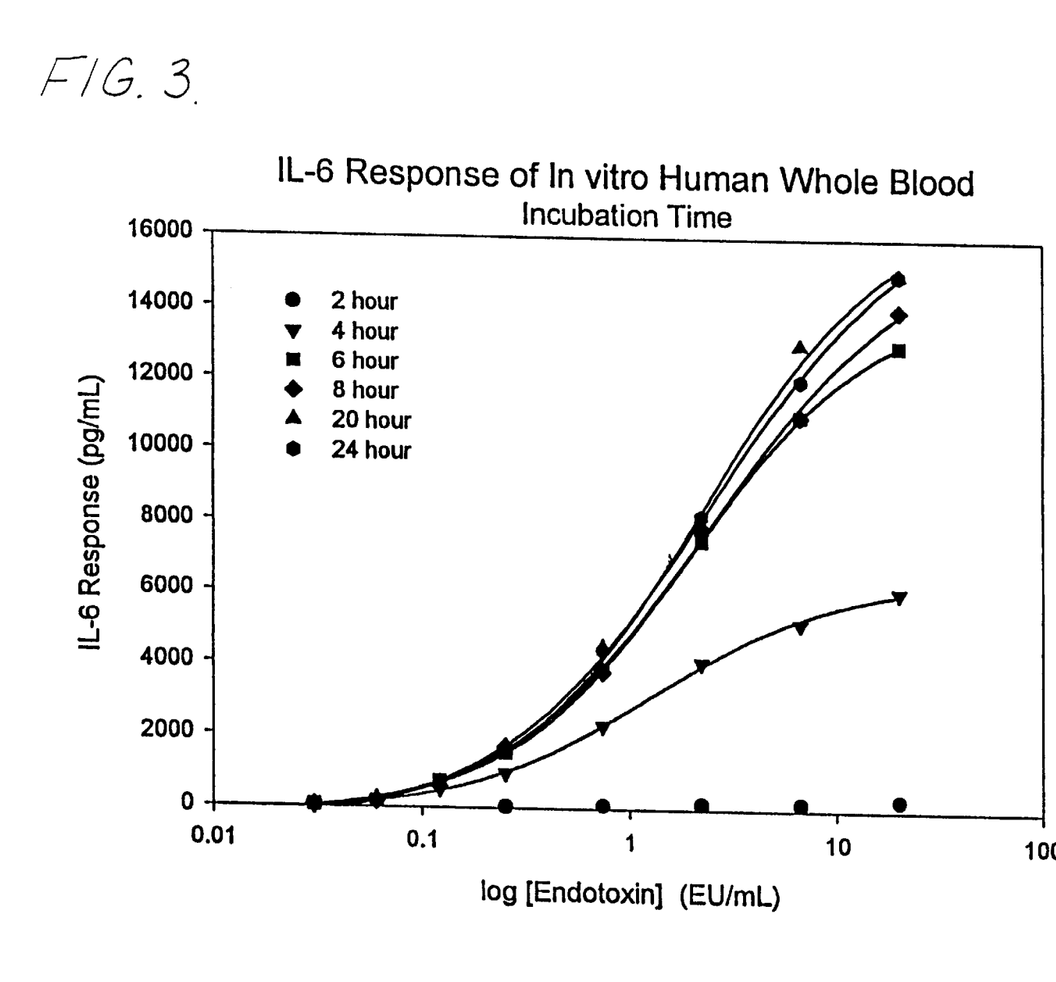
FIG. 3: A chart of the IL-6 response of ex vivo whole human blood stimulated with USP endotoxin as described in Example 4. Blood from a single donor, final volume about 20%, was used. This chart shows the effect of incubation time on the final concentration of IL-6 for various endotoxin concentrations. After about 6 hours, minimal additional IL-6 is generated by the monocytes in the whole blood solution. Significant amounts of IL-6 are generated at all concentrations after a 4 hour incubation period. A 2 hour incubation period does not generate desirable levels of IL-6.

Results are shown in FIG. 3. After about 6 hours, minimal additional IL-6 is generated by the monocytes in the whole blood solution. Significant amounts of IL-6 are generated at all concentrations after a 4 hour incubation period. A 2 hour incubation period is insufficient to generate detectable levels of IL-6. Thus, a 4 hour incubation period is sufficient to produce detectable levels of IL-6 in a useful range of endotoxin concentrations.

Example 5

Comparison of the Two Plate Assay of U.S. Pat. No. 5,891,728 and the One Plate Assay of the Present Invention The "one plate" test was carried out as in Example 2, except that final whole blood concentration was about 20% in the test volume, and human serum albumin (HSA) was used instead of DCLHb® in the "test samples," and a 4 hour incubation time was used.

For comparison, the "two plate" test described in U.S. Pat. No. 5,891,728 was carried out as follows on buffer standards and HSA samples spiked with the same amount of endotoxin:

Whole human blood (diluted to 20% with RPMI) was stimulated with endotoxin (USP, 2000 EU/ml) for 4 hours. Test samples were pyrogen-free human serum albumin (HSA, 4.5%, 'unspiked') spiked with endotoxin at 2.5 and 10 EU/ml and then diluted 1/10 to give 0.25 and 1.0 EU/ml 'final' concentrations for testing.

Incubation volumes were as follow: For STD curve: 250 µl RPMI+200 µl blood+100 µl endotoxin dose+450 µl RPMI=1 ml total vol./well. For samples: 250 µl RPMI+200 µl blood+100 µl HSA unspiked/spiked with endotoxin+450 µl RPMI=1 ml total vol./well.

Standards and samples were added in triplicate or quadruplicate to 48-well plates and cultured with 20% blood at 37° C. for 4 hours in an atmosphere of 5% $CO_2$ in air. At the end of the incubation, aliquots of the culture fluids (cell-conditioned media) were taken for ELISA of IL-6 (see Taktak et al., 1991).

Results comparing the IL-6 sensitivity of the one plate and two plate assays are shown in FIG. 4. As shown by these results, the one plate assay is much more sensitive than the two plate assay, when performed under similar conditions. In addition, "spike recovery" of the endotoxin signal in the HSA samples, or the amount of IL-6 production that is maintained in the HSA samples as compared to RPMI samples with an equal amount of endotoxin, is better in the one-plate assay of the present invention than in the previously disclosed two-plate assay.

Example 6

Comparison of Cytokine Production in Whole Blood in the Two Plate Assay of U.S. Pat. No. 5,891,728

Figure 5:
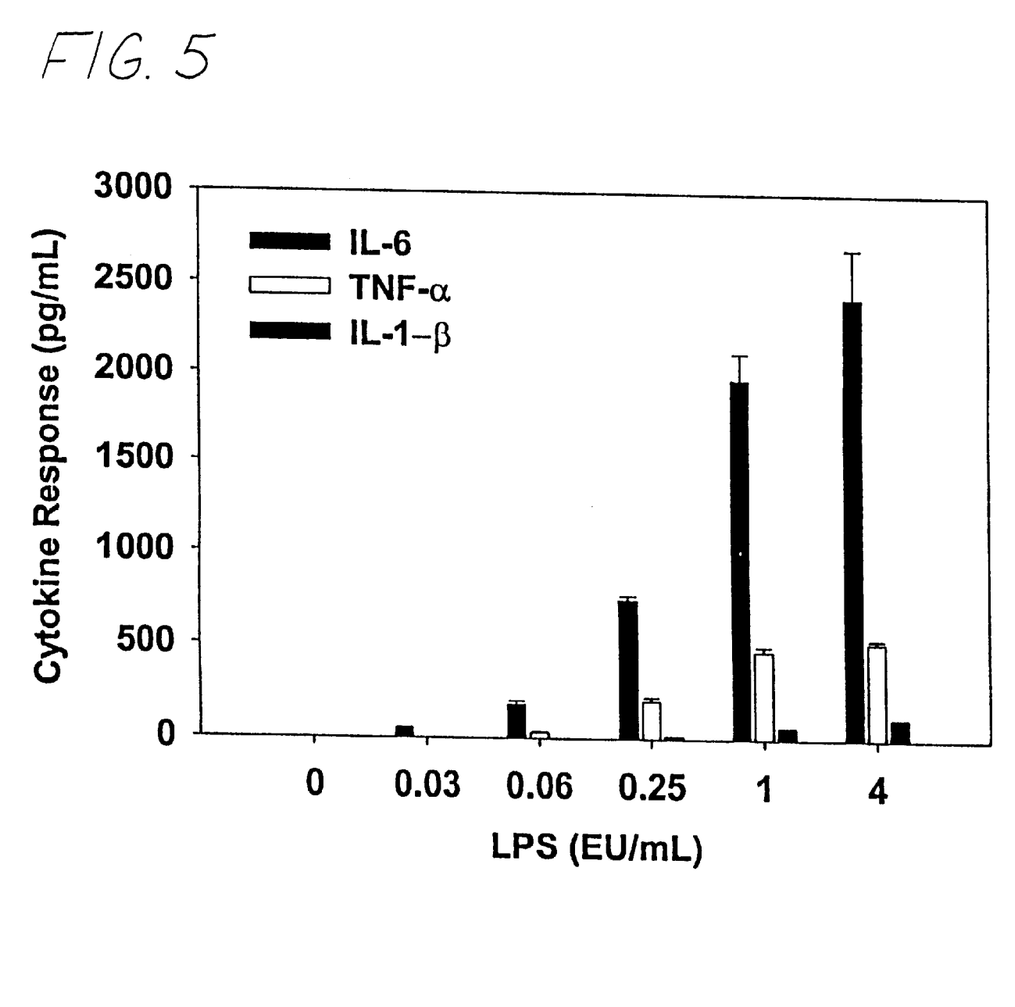
FIG. 5: A chart of the IL-6, TNF $\alpha$, and IL-1 $\beta$ responses of ex vivo whole human blood stimulated with USP endotoxin as described in Example 6. Blood from a single donor was diluted to a final concentration of about 20%, and an incubation time of 4 hours was used. This chart compares the amounts of cytokines released in the "two plate" assay described in U.S. Pat. No. 5,891,728 in a 4 hour period.

The two plate assay was carried out as described in Example 5, except that TNFα and IL-1 β were also quantified in addition to IL-6. TNF α was assayed as described in Meager et al., "Preparation and characterization of monoclonal antibodies directed against antigenic determinants of recombinant human tumour necrosis factor (rTNF)" Hybridoma, 6:305–311 (1987), and IL-1 β was assayed using a matched pair of monoclonal anti-IL-1 β antibodies from R&D Systems, or an IL-1 β ELISA kit provided by DPC Biermann, both of which gave broadly similar results. The results of the experiment are shown in FIG. 5. As can be seen from these results, IL-6 is produced in relatively large amounts, and is easily detectable in the 4 hour incubation time. In contrast, TNF α and IL-1 β are release in lesser amounts by the whole blood culture when incubated with endotoxin.

Four hour blood cultures in the absence of added endotoxin contained concentrations of immunoreactive TNF α and IL-1 β at or below the detection limits of the ELISAs used to detect them. In contrast, concentrations of immunoreactive IL-6 were detectable in these cultures. In healthy donors, concentrations of immunoreactive IL-6 were below 200 pg/ml (usually below 100 pg/ml) but in donors who had recently recovered from minor viral infections (e.g. common colds) or bacterial infections (of the gingiva or gut) basal (i.e. unstimulated) concentrations of IL-6 sometimes exceeded 200 pg/ml and responses to added endotoxin were smaller than for the blood of healthy donors. Consequently, the choice of IL-6 as the measured variable enables the identification and 'screening out' of donors who are not entirely well, even though they may feel well enough to serve as a blood donor for the in vitro pyrogen test. The measured basal levels of immunoreactive IL-6 did not diminish the sensitivity of tests using IL-6 as the measured variable, rather than TNF α or IL-1 β, since the choice of IL-6 yielded the most sensitive test system (see FIG. 5). Thus, IL-6 was chosen for testing in the present invention. However, TNF α or IL-1 β would also be suitable for use as the quantified cytokine of the present invention.

Example 7

Assay of Pyrogen Content in Samples Spiked with Endotoxin (LPS and LOS): Comparison of Whole Blood Reagent Donors Whole human blood (diluted, to give about 50% blood in final test volume, with RPMI) from two healthy donors was stimulated with endotoxin (either LPS or LOS, as indicated) to produce IL-8. LOS, pyrogenic lipooligosaccharide, utilized in the study is from *Neisseria meningitidis* and is distinguished from LPS by its highly-branched basal oligosaccharide structure and the absence of repeating O-antigen subunits. The blood was incubated with endotoxin for approximately four hours and IL-8 production was measured by ELISA. In other respects, the test was carried out as set forth in Example 3.

Figure 6:
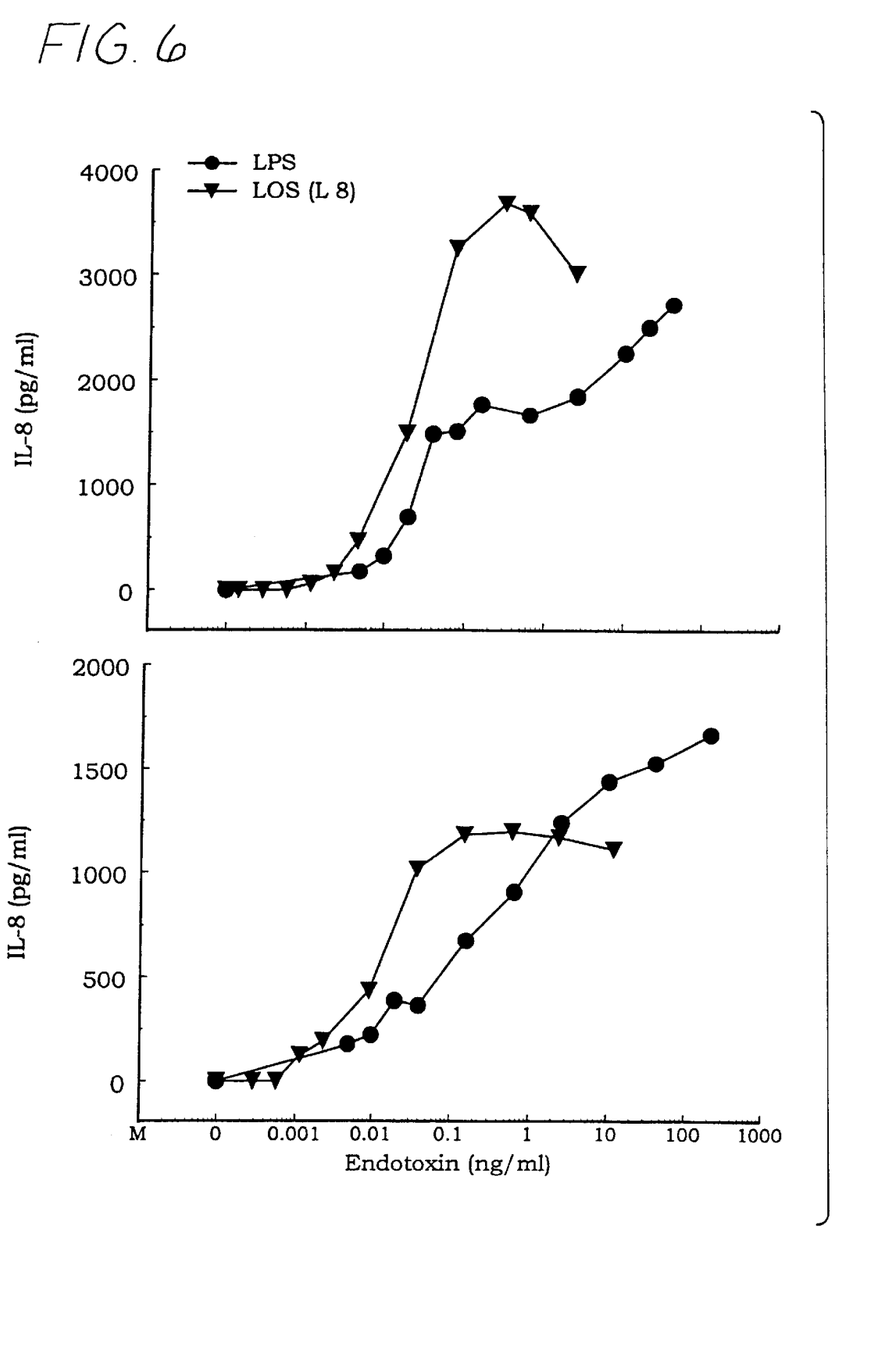
FIG. 6: A chart of the IL-8 response of ex vivo whole human blood stimulated with LPS or LOS endotoxin as described in Example 7. Blood from two donors was diluted to a final concentration of about 50%, and the samples were incubated for four hours. This chart shows the donor effect on the test method of the present invention. Although the absolute amount of IL-8 generated by whole human blood incubations from different donors varies considerably, the shape of the dose-response curve is very similar for both donors. This chart illustrates the importance of generating a standard curve from known endotoxin concentrations in order to interpret the data generated by the method of the invention, or by any method which utilizes whole human blood as a reagent.

Results are shown in FIG. 6. Although the absolute amount of IL-8 generated by the whole human blood incubations from different donors varies considerably, the shape of the dose-response curve is very similar for both donors. The whole blood from both donors produced a measurable IL-8 response when incubated with either endotoxin. However, it is notable that stimulation with the endotoxin LOS resulted in production of higher concentrations of IL-8 in response to lower endotoxin concentrations compared to IL-8 production in response to LPS stimulation. These results clearly indicate that the cytokine IL-8 may be employed to detect pyrogens in a sample in accordance with the method of the invention.

The invention being thus described, it will be obvious that the same can be modified in various ways. Such variations are not to be regarded as a departure from the spirit and scope of the present invention, and all such modifications and equivalents as would be obvious to one skilled in the art are intended to be included without the scope of the following claims.

We claim:

1. A method of detecting pyrogens in a sample comprising the steps of:
   a) combining a pyrogen-free monocyte-containing reagent and the sample to be tested in a pyrogen-free assay system, wherein the assay system comprises at least one surface treated with a pyrogen-free antibody to a cytokine; and
   b) assaying the assay system for the presence of cytokine bound to the antibody on the surface; whereby an elevated level of cytokine bound to the surface indicates the presence of pyrogens in the sample tested.

2. The method of claim 1 wherein the monocyte-containing reagent comprises whole blood.

3. The method of claim 2 wherein the monocyte-containing reagent further comprises a diluent.

4. The method of claim 2 wherein the monocyte-containing reagent further comprises an anticoagulant.

5. The method of claim 4 wherein the monocyte-containing reagent further comprises a diluent.

6. The method of claim 3 wherein the diluent is RPMI media.

7. The method of claim 2 wherein the whole blood is human whole blood.

8. The method of claim 1 wherein the cytokine is selected from the group consisting of interleukin-1, interleukin-1ra, interleukin-6, interleukin-8, tumor necrosis factor-$\alpha$.

9. The method of claim 8 wherein the cytokine is interleukin-6.

10. The method of claim 1 wherein the assay system includes at least one microtiter well, and the surface on which the antibody is applied is a portion of the interior of the microtiter well.

11. The method of claim 10 wherein the microtiter well is made from polystyrene or polypropylene.

12. The method of claim 1 wherein the assay system is assayed by a colorimetric enzyme-linked immunosorbent assay for the cytokine.

13. The method of claim 1 wherein the assay system is assayed by a radio-labeled immunoassay for the cytokine.

14. The method of claim 1 wherein the assay system is assayed by a fluorescence-labeled immunoassay for the cytokine.

15. The method of claim 1 wherein the pyrogen-free antibody is a polyclonal antibody.

16. The method of claim 1 wherein the pyrogen-free antibody is a monoclonal antibody.

17. The method of claim 1 wherein the sample is a medicinal drug for injection or infusion.

18. The method of claim 1 wherein the sample is a blood product.

19. A method of detecting pyrogens in a sample comprising the steps of:
   a) combining a pyrogen-free monocyte-containing reagent and the sample to be tested in a pyrogen-free assay system, wherein the assay system comprises at least one surface treated with a pyrogen-free antibody to an endogenous mediator of the inflammatory response; and
   b) assaying the assay system for the presence of the mediator bound to the antibody on the surface; whereby an elevated level of the mediator bound to the surface indicates the presence of pyrogens in the sample tested.

20. The method of claim 19 wherein the endogenous mediator of the inflammatory response is endothelin.

* * * * *